United States Patent
Cifter et al.

(10) Patent No.: US 8,563,035 B2
(45) Date of Patent: *Oct. 22, 2013

(54) ORAL TABLET COMPOSITIONS OF DEXLANSOPRAZOLE

(75) Inventors: Umit Cifter, Istanbul (TR); Ali Turkyilmaz, Istanbul (TR); Ibrahim Murat Uzer, Istanbul (TR); Alper Terkinli, Istanbul (TR); Levent Oner, Ankara (TR)

(73) Assignee: Sanovel Ilac Sanayi Ve Ticaret Anomin Sirketi

( * ) Notice: Subject to any disclaimer, the term of this patent is extended or adjusted under 35 U.S.C. 154(b) by 0 days.

This patent is subject to a terminal disclaimer.

(21) Appl. No.: 13/101,319

(22) Filed: May 5, 2011

(65) Prior Publication Data

US 2011/0274754 A1    Nov. 10, 2011

(30) Foreign Application Priority Data

May 5, 2010    (TR) .............................. a 2010 03557
Aug. 23, 2010  (TR) .............................. a 2010 07007

(51) Int. Cl.
*A61K 9/22*    (2006.01)
(52) U.S. Cl.
USPC .......................................... 424/468; 514/338
(58) Field of Classification Search
None
See application file for complete search history.

(56) References Cited

U.S. PATENT DOCUMENTS

| 2006/0165797 A1 | 7/2006 | Plachetka | |
| 2007/0071811 A1* | 3/2007 | Kadosh et al. | 424/464 |
| 2008/0260818 A1* | 10/2008 | Penhasi et al. | 424/457 |
| 2009/0098199 A1* | 4/2009 | Lee et al. | 424/451 |
| 2009/0263475 A1* | 10/2009 | Manne et al. | 424/451 |

FOREIGN PATENT DOCUMENTS

| EP | 1 967 184 A1 | 9/2008 |
| WO | 2006/049565 A1 | 5/2006 |

OTHER PUBLICATIONS

Extended European Search Report dated Feb. 1, 2012 in European Patent Application No. 11164758.2.
Extended European Search Report dated Dec. 9, 2011 in European Patent Application No. 11164774.9.
Harianawala, A. et al., "Measurement of pH 1-10 near dissolving enteric coatings," International Journal of Pharmaceutics, vol. 247, 2002, pp. 139-146.
Metz et al., "Review Article: dual delayed release formulation of dsxlansoprazole MR, a novel approach to overcome the limitations of conventional single release proton pump inhibitor therapy," Alimentary Pharmacology & Therapeutics, Blackwell Scientific Publications Ltd., Cambridge, GB, vol. 29, No. 9, May 1, 2009, pp. 928-937.
Search Report and Written Opinion dated Mar. 1, 2011 in Turkish Patent Application No. TR201006225, filed Jul. 28, 2010.
Search Report and Written Opinion dated Mar. 2, 2011 in Turkish Patent Application No. TR201007007, filed Aug. 23, 2010.

\* cited by examiner

*Primary Examiner* — David J Blanchard
*Assistant Examiner* — Daniel F Coughlin
(74) *Attorney, Agent, or Firm* — Kenyon and Kenyon LLP

(57) ABSTRACT

Oral tablet compositions of dexlansoprazole or pharmaceutically acceptable salts or hydrated forms thereof having a gradual release and processes for the manufacture of the tablet composition and its use in the treatment of gastrointestinal disorders.

15 Claims, No Drawings

ORAL TABLET COMPOSITIONS OF DEXLANSOPRAZOLE

CROSS REFERENCE TO RELATED APPLICATIONS

This application is based upon Turkish Patent Application No. TR201003557, filed May 5, 2010 and Turkish Patent Application No. TR201007007 filed Aug. 23, 2010, under relevant sections of 35 USC §119, the entire contents of each application being incorporated by reference herein.

FIELD OF THE INVENTION

The present invention relates to oral tablet compositions of dexlansoprazole or pharmaceutically acceptable salts or hydrated forms thereof having a gradual release and furthermore directed to processes for the manufacture of the tablet composition and its use in the treatment of gastrointestinal disorders.

BACKGROUND OF THE INVENTION

The active ingredient, dexlansoprazole is the R-enantiomer of lansoprazole which inhibits gastric acid secretion (a proton pump inhibitor). Its chemical name is (+)-2-[(R)-{[3-methyl-4-(2,2,2-trifluoroethoxy)pyridin-2-yl]methyl}sulfinyl]-1H-benzimidazole and its chemical structure is shown in the following Formula I.

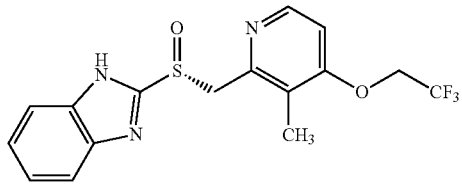

Formula I

Delayed release capsule form of dexlansoprazole is currently marketed and it is administered orally in a therapeutic dose of 30 mg and 60 mg.

As in other benzimidazole compounds, dexlansoprazole has also poor stability and is unstable to acidic medium, humidity, light and sensitive to heating. When orally administrated, it may not be able to sufficiently activate since it is decomposed by gastric acid and the like. Thus, several problems occur in formulating this compound into oral pharmaceutical dosage forms because of the acidic environment of the stomach. In particular, it will be rapidly decomposed and change color under moist conditions or in acidic to neutral aqueous solution.

When these compounds are formulated into pharmaceutical preparations for oral administration, they require special techniques to avoid contact of drug with the gastric acid of the stomach. One technique most commonly used is to coat these compounds, or its granules or pellets, with an enteric coating. However, the material used in enteric coatings itself is acidic, which can cause the decomposition of the compound. Such decomposition occurs even during the enteric coating process, which results in the coloration of the surface of the drug-containing core.

On the other hand, enteric films do not show high flexibility so that compression stress can yield rupturing of the film. It is therefore necessary to use a tableting technique that endorses the compression strain and maintains the acid resistance of the formulation after compression of the granules. Therefore caution is needed to be taken while compressing the powders and granules to form a tablet dosage form. Such a formulation has to be compressed to a specific hardness.

In the prior art, there are many patents including benzimidazoles such as lansoprazole and its R-enantiomer, dexlansoprazole in several different pharmaceutical compositions. Crystal form of R-lansoprazole is described in EP-B1-1129088.

Thus, there is still a need for developing pharmaceutical formulations of dexlansoprazole wherein good stability is achieved in a technologically simple way including an improved manufacturing process which overcomes the above described problems and provides a bioavailable pharmaceutical composition according to the formulations currently used.

The pharmaceutical formulation of this invention advantageously provides a tablet dosage form which is bioequivalent to a capsule dosage form of the same or substantially similar strength. The tablet dosage form can further be advantageous in that the manufacturing process can require fewer steps, e.g., eliminate the need for pellet formation and/or coating of those pellets, and there is no need for the additional expense of providing capsule shells.

Further advantages and embodiments of the present invention will become apparent from the following description.

SUMMARY AND DESCRIPTION OF THE INVENTION

The main object of the present invention is to provide stable oral tablet compositions of dexlansoprazole or pharmaceutically acceptable salts or hydrated forms thereof having gradual release previously undisclosed in the prior art which overcomes the above described problems and have additive advantages over them.

Another object of the present invention is to express a pharmacological effect of the active ingredient stably and rapidly after administration and sustaining pharmacological effect of gradual release for a prolonged period of time and to have a desired release profile, wherein the release of the active ingredient, dexlansoprazole, is controlled in two steps, and the active ingredient is released in the gastrointestinal tract over a long period of time. In the prior art, this sustained release is obtained mostly with using different enteric coatings comprising different polymers which dissolves in different pH. Because when the granules comprising the active ingredient first reach the proximal small intestine has a rapid release at pH 5.5 and the rest dissolves distally in the small intestine at pH 6.5 to obtain the prolonged release.

Yet another object of the present invention is to provide an improved and simple process for preparing the oral tablet composition of dexlansoprazole or pharmaceutically acceptable salts or hydrated forms thereof having a gradual release.

In this invention, gradual release means that having a two step release profile in a prolonged time. In a first step, 5.0% to 40.0% of dexlansoprazole is released rapidly in its powder form from the oral tablet composition and has a stable effect up to 4 hours in proximal small intestine at pH 5.5. In a second step, the remainder of the dexlansoprazole (60.0 to 95.0%) is released in a prolonged way in its granulated form from the oral tablet composition in the small intestine at pH 6.0 to 6.5.

Surprisingly, we obtained this prolonged effect with gradual release of dexlansoprazole only using lactose and microcrystalline cellulose in the granulation step of the oral tablet compositions of dexlansoprazole or pharmaceutically acceptable salts or hydrated forms thereof. More specifically, the weight ratio of lactose to microcrystalline cellulose in dexlansoprazole granule is between 1:20 and 1:5 by weight, preferably it is 1:9 by weight. Furthermore, the granules are comprised of talc, colloidal silicon dioxide, magnesium stearate, hydrophobic and/or hydrophilic agents, an alkali compound, binders or their mixtures.

In other words, the desired gradual release is achieved by not using pH dependent different coatings. This also prevents the dose dumping of the active ingredient which can be a serious problem caused by the wrong design of the modified release formulations.

Dose dumping is one of the most important disadvantages of modified release dosage forms. For several different reasons it is difficult to develop modified release formulations, such as those having a gradual release profile tablet formulations although there are many modified release formulations formulated with different coatings or using rate controlling agents. First of all, modified release formulations of these medicaments can be prone to "dose dumping" in which the release of the active ingredient is delayed but once the release begins the medicament may released rapidly. The most important critical factor of dose dumping is the amount of the active substance released in early time point. Therefore, the active ingredient concentration in the plasma will increase suddenly and this may lead to toxicity.

According to the main object of the present invention, the oral tablet composition of dexlansoprazole or pharmaceutically acceptable salts or hydrated forms thereof having a gradual release is characterised in that said tablet comprises:
  a) 5.0 to 40.0% of dexlansoprazole in powder form;
  b) 60.0 to 95.0% of dexlansoprazole granule comprising lactose, microcrystalline cellulose, a hydrophobic and/or hydrophilic agent, an alkali compound, binders or their mixtures; and
  c) a single enteric coating that dissolves at between pH 5.5 and 6.4.

In one embodiment, the single enteric coating dissolves preferably at between pH 6.0 and 6.4.

According to another object of this present invention, to have a desired release profile and an improved stability and maximize the mechanical resistance of the tablets, this oral tablet formulation having a gradual release has been designed to compress in a specific hardness to form tablets wherein the compression force of the powder and granule mixture of dexlansoprazole is between 2 to 30 kN, preferably between 3 to 12 kN.

According to a main object of the present invention, the hydrophobic and/or hydrophilic agents in the dexlansoprazole granule wherein the amount is in between 60.0 to 95.0% by weight, are selected from the group comprising hydrogenated vegetable oils such as hydrogenated castor oil; glyceryl behenate, wax, wax-like substance, fats, oils, fatty acid, fatty alcohol, shellac, pullulan, agar, gellan gum, guar gum, carageenan, acacia gum, gum arabic, dextran, pectin and their mixtures, preferably the hydrophobic agent is hydrogenated vegetable oils, such as hydrogenated castor oil.

In one embodiment, the single enteric coating of the tablet that dissolves between at pH 5.5 and 6.4 is selected from the group comprising of cellulose acetate phthalate, cellulose acetate succinate, hydroxpropyl cellulose phthalate, hydroxpropyl ethylcellulose phthalate, hydroxylpropyl methyl cellulose phthalate, hydroxylpropyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac and polymethacrylate copolymers such as methacrylic acid-ethyl acrylate copolymer, methacrylic acid-methyl methacrylate copolymer or mixtures thereof.

In one embodiment, the amount of the single enteric coating layer is between 1% and 50% (w/w) of the total weight of the tablet; preferably it is 5% to 30% (w/w).

According to one embodiment, the amount of dexlansoprazole or pharmaceutically acceptable salts or hydrated forms thereof is from 5% to 50% by weight of the total tablet.

Yet another embodiment of the invention is to have a film coating under the enteric coating of the tablet so as to prevent any problems which may occur during the tablet's shelf-life. The film coating layer is selected from the group comprising of polyvinyl alcohol, polyvinylpyrrolidone (PVP), hydroxypropyl cellulose, lowsubstituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols (such as D-mannitol, erythritol, etc) or mixtures thereof.

The oral tablet composition of this invention comprise one or more pharmaceutically acceptable excipients selected from the group comprising binders, diluents and/or fillers, lubricants, glidants, disintegrants, basic stabilizers, coloring agents or flavoring agents.

Suitable binders may comprise but are not limited to methyl cellulose, ethyl cellulose, hydroxypropyl methyl cellulose, hydroxypropyl cellulose, sodium carboxymethyl cellulose, polyvinyl pyrrolidone, polyvinyl alcohol, polymethacrylates, starch, gelatin, alginic acid, sucrose and the like and mixtures thereof.

Suitable diluents and/or fillers may comprise but are not limited to microcrystalline cellulose, cellulose, lactose, starch, calcium phosphates, calcium sulphates, mannitol, glucose, sucrose, sorbitol and the like and mixtures thereof.

Suitable lubricants may comprise but are not limited to stearic acid, magnesium, calcium or sodium stearate, sodium stearyl fumarate, talc, waxes, liquid paraffin, and the like and mixtures thereof.

Suitable glidants may comprise but are not limited to talc, aluminium silicate, colloidal silicon dioxide, starch and the like and mixtures thereof.

Suitable disintegrants may comprise but are not limited to alginic acid and salts, sodium carboxymethyl cellulose, hydroxypropyl methyl cellulose, starch, sodium starch glycolate, crosslinked polyvinyl pyrrolidone and the like and mixtures thereof.

The oral tablet compositions of this invention are administrated once-a-day or twice-a-day.

In one embodiment, the oral tablet compositions of dexlansoprazole or pharmaceutically acceptable salts or hydrated forms thereof having a gradual release of this invention is obtained by the in vitro dissolution profiles tested.

In this present invention, surprisingly the problem is also solved by a more efficient process to prepare a gradual release oral tablet composition of dexlansoprazole or pharmaceutically acceptable salts or hydrated forms thereof comprising the following steps:
  a) 5.0 to 40.0% of dexlansoprazole is separated in its powder form;

b) 60.0 to 95.0% of dexlansoprazole is blended in a powder blender with lactose and microcrystalline cellulose, an alkali compound, a hydrophobic and/or hydrophilic agent and binder;

c) this powder mix (step b) is then granulated using water, ethanol or an ethanol-water mixture;

d) wet granules are sieved and dried at a temperature not exceeding 45° C.;

e) the granules are then sieved to obtain a maximum size of 500 μm;

f) the granules are optionally blended with other excipients, such as magnesium stearate, colloidal silicon dioxide or talc;

g) dexlansoprazole (step a) in powder form is added to this granules and blended together until a homogenous powder mixture is obtained;

h) resulting powder is compressed into tablets;

i) the tablets are optionally precoated with a protective layer; and j) a single enteric coating that dissolves between at pH 5.5 and 6.4, is then applied to the precoated tablets.

The oral tablet composition of dexlansoprazole or pharmaceutically acceptable salts or hydrated forms thereof having a gradual release is used for the treatment of gastrointestinal disorders.

As apparent from the example below, by the method of the present invention the hardness of the tablet is improved. In addition, dissolution and stability is also improved.

This invention is further defined by reference to the following example. Although the example is not intended to limit the scope of the present invention, it should be considered in the light of the description detailed above. It will be apparent to those skilled in the art that many modifications, both to materials and methods, may be practiced without departing from the scope of the invention.

Example 1

| Ingredients | Amount (%) |
| --- | --- |
| dexlansoprazole | 5.0-50.0 |
| lactose monohydrate | 10.0-95.0 |
| microcrystalline cellulose | 1.0-85.0 |
| magnesium oxide | 0.0-5.0 |
| talc | 0.0-10.0 |
| colloidal silicon dioxide | 0.0-10.0 |
| magnesium stearate | 0.0-15.0 |
| hydrogenated castor oil | 0.0-20.0 |
| Total | 100.0 |

Dexlansoprazole is blended in a powder blender until an adequate homogenous powder form is obtained and 5.0 to 40.0% of it remains in powder form. The remainder of it (60.0 to 95.0%) is blended together with lactose and microcrystalline cellulose in a dry powder blender for about 20 minutes, then an alkali compound, hydrophobic and/or hydrophilic agent and binder is added to this mixture and blended again. This powder mix is then granulated using water, ethanol or an ethanol-water mixture and wet granules are sieved and dried at a temperature not exceeding 45° C. These granules are then sieved to obtain a maximum granule size of 500 μm. These granules are then blended with the rest of dexlansoprazole (5.0 to 40.0%) powder and optionally with other excipients such as magnesium stearate, colloidal silicon dioxide or talc. The powder is then compressed into slugs using suitable compression equipment and compression strength. The final blend is then compressed into tablets with a rotary tablet press using a compression strength of about 5 to 10 kN. These tablets are then coated in a pan coater with the aforementioned enteric coating that dissolves between at pH 5.5 and 6.4 and optionally coated with a protective layer coating up to an approximate weight gain of about 10%.

The invention claimed is:

1. An oral tablet of at least one of dexlansoprazole, pharmaceutically acceptable salts and hydrates thereof and having a gradual release, wherein said tablet comprises:
   a) 5.0 to 40.0% by weight of the dexlansoprazole in powder form;
   b) 60.0 to 95.0% by weight of the dexlansoprazole in granule form comprising the dexlansoprazole, lactose and microcrystalline cellulose, and wherein a weight ratio of lactose to microcrystalline cellulose in said dexlansoprazole granule form is between 1:20 and 1:5 by weight; and
   c) a single enteric coating that dissolves at between pH 5.5 and 6.4,
wherein the tablet has a release profile if orally administered in that the dexlansoprazole is gradually released after administration first in the proximal small intestine at pH 5.5 and then in the distal small intestine at pH 6.0 to 6.4.

2. The oral tablet according to claim 1, wherein a compression force to form the tablet is between 2 to 30 kN.

3. The oral tablet according to claim 1, wherein a compression force to form the tablet is between 3 and 12 kN.

4. The oral tablet according to claim 1, wherein the weight ratio of lactose to microcrystalline cellulose in said dexlansoprazole granule form is about 1:9 by weight.

5. The oral tablet according to claim 1, wherein said 60.0 to 95.0% of dexlansoprazole granule further comprises at least one compound selected from a hydrophobic agent, a hydrophilic agent, an alkali compound and a binder.

6. The oral tablet according to claim 5, wherein the hydrophobic agent is selected from hydrogenated vegetable oils such as hydrogenated castor oil, glyceryl behenate, wax, wax-like substance, fats, oils, fatty acid, fatty alcohol, shellac, and their mixtures, and the hydrophilic agent is selected from pullulan, agar, gellan gum, guar gum, carageenan, acacia gum, gum arabic, dextran, pectin and their mixtures.

7. The oral tablet according to claim 1, wherein the single enteric coating that dissolves at between pH 5.5 and 6.4 comprises cellulose acetate phthalate, cellulose acetate succinate, hydroxypropyl cellulose phthalate, hydroxypropyl ethylcellulose phthalate, hydroxyl propyl methyl cellulose phthalate, hydroxyl propyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac and polymethacrylate copolymers such as methacrylic acid-ethyl acrylate copolymer, methacrylic acid-methyl methacrylate copolymer or mixtures thereof.

8. The oral tablet according to claim 1, wherein the amount of the enteric coating is between 1% and 50% (w/w) of the total weight of the tablet.

9. The oral tablet according to claim 7, wherein the amount of the enteric coating is between 1% and 50% (w/w) of the total weight of the tablet.

10. The oral tablet according to claim 1, wherein the amount of the enteric coating is between 5% to 30% (w/w) of the total weight of the tablet.

11. The tablet according to claim 7, wherein the amount of the enteric coating is between 5% and 30% (w/w) of the total weight of the tablet.

12. The oral tablet according to claim 1, further comprising a film coating under the enteric coating.

13. The oral tablet according to claim 12, wherein the film coating comprises polyvinyl alcohol, polyvinylpyrrolidone (PVP), hydroxypropyl cellulose, low substituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols (such as D-mannitol, erythritol, etc) or mixtures thereof.

14. The oral tablet according to claim 1, in which said tablet is configured to be ingested for use in the treatment of gastrointestinal disorders.

15. The oral tablet according to claim 5, wherein the at least one compound is selected from a hydrophobic agent, a hydrophilic agent and mixtures thereof.

* * * * *